United States Patent [19]
Richardson

[11] 3,981,973
[45] Sept. 21, 1976

[54] CRYSTAL GROWTH IN THE PRESENCE OF FINELY DIVIDED POLYTETRAFLUOROETHYLENE

[75] Inventor: John G. Richardson, Cleveland, Ohio

[73] Assignee: The Harshaw Chemical Company, Cleveland, Ohio

[22] Filed: Dec. 17, 1973

[21] Appl. No.: 425,320

[52] U.S. Cl............................ 423/265; 423/266; 423/268; 423/551; 423/597; 23/300; 23/302 R
[51] Int. Cl.² ................. C01D 13/00; C01D 5/00; C01G 1/00
[58] Field of Search ........... 423/266, 268, 265, 597, 423/551; 23/300, 302

[56] References Cited
UNITED STATES PATENTS

| 3,197,289 | 7/1965 | Rogers | 423/266 X |
| 3,240,558 | 3/1966 | Heiss et al. | 423/268 |
| 3,770,390 | 11/1973 | Teot | 423/551 X |

Primary Examiner—Edward Stern
Attorney, Agent, or Firm—Alfred D. Lobo

[57] ABSTRACT

Metal salts which are crystallizable from a saturated aqueous solution of the salt in the presence of a dispersion of polytetrafluoroethylene (hereinafter referred to as PTFE) resin are grown as geometrically better defined and larger crystals than those grown from an unseeded saturated solution.

3 Claims, No Drawings

CRYSTAL GROWTH IN THE PRESENCE OF FINELY DIVIDED POLYTETRAFLUOROETHYLENE

BACKGROUND OF THE INVENTION

Crystals are rarely pure because they generally contain small quantities of foreign matter which have been built-in or occluded. Gases, liquids and solids are readily occluded in a growing crystal; dirt, air and mother liquor are the most common occlusions found in commercial crystals. From the commercial crystallization point of view, the main interest lies in finding methods to prevent such occlusions from occurring. Vapor occlusions are minimized by avoiding vigorous agitation or boiling. The application of ultrasonic radiation to the system is also used to prevent bubbles or particles from adhering to a growing crystal face. Most importantly, the crystallizing system is kept clean to avoid dirt, other debris and particularly organic contaminants from being occluded into a crystal.

This invention is oppositely directed; that is, this process deliberately provides fine PTFE contaminant particles, in the size range from about 0.05 micron to about 0.5 micron in diameter, as seeds to facilitate the formation and growth of desirable large crystals in which the seeds are beneficially occluded.

Crystallization comprises three fundamental steps: supersaturation (or super cooling), formation of crystal nuclei, and the subsequent growth of these nuclei into crystals. Supersaturation may be achieved by cooling, evaporation of the solvent, addition of a precipitating agent, as a result of the chemical reaction, etc., and is vital in any industrial crystallizing operation. However, supersaturation alone is not sufficient to cause crystals to grow. Before the growth stage can commence, there must exist in the system a number of tiny crystal embryos or nuclei. These may be formed spontaneously, induced artificially, or deliberately added.

One of the best known methods of inducing crystallization is that of seeding, that is, the deliberate addition of tiny crystals to the super cooled system. The seeds do not necessarily have to consist of the material to be crystallized; crystals of some isomorphous substances will often work. In some cases, inert crystalline particles can give the desired effect. Super cooled systems are sometimes seeded accidentally by atmospheric dust, but such seeding does not produce the results of seeding with finely divided PTFE.

It is also well-known that the accidental production of nuclei, referred to as 'false grain', should not be permitted in an industrial crystallizer. This is undesirable, not for the mass of material precipitated, which may be relatively small, but for the number of seeds which are produced. In any case, it is well-known that if controlled growth is required, accidental nucleation must be avoided or counter-acted, and extreme precautions must be taken to get rid of false grain where conventional precautions fail. The deliberate introduction of any contaminant particles, particularly organic particles of a synthetic polymeric resin, is contrary to recognized commercial crystallization practice.

Crystals of a given substance, produced by different methods, may be completely different in physical appearance, even though they belong to the same crystallographic system. This variation in external form is called a modification of habit and it results from the inhibition of growth in one direction or the enhancement of growth in another. The most common cause of habit modification is the presence of impurities; these are absorbed on certain crystal faces and stunt the growth in those directions. Many complex dyes act as habit modifiers for inorganic salts and their habit-modifying power depends on their anionic or cationic nature. Selected surface active agents also have been found useful for habit-modification purposes. Surprisingly, in general, the process of this invention has no noticeable stunting effect. Quite to the contrary, crystals are grown by this process which are generally uniformly well-defined and larger than crystals grown without seeding with the PTFE particles, irrespective of the particular type of industrial crystallizer used. Crystals of particular lattice structure appear to be more susceptible to the beneficial effects of this process than others, but surprisingly I have found no inorganic ionic salt crystals which are detrimentally affected by deliberate seeding, in the specified preferred ranges, with a dispersion of PTFE resin particles.

Again, it is known that various relationships have been proposed for theoretically predicting the mass deposition rates on crystal faces, and these relationships have been used to predict geometrically regular crystal shapes, the size of a crystal after it has remained in a crystallizing medium for a fixed period of time, and the like. The crystallization process of the instant invention does not appear to be characterized by any known mathematical relationship, and in fact, there appears to be no simple method of predicting with accuracy the effect of seeding even in crystals of the same lattice structure.

While it is clearly advantageous to produce crystals as large as possible, their actual size is only of secondary importance; what really matters, with relatively large crystals, is the regularity of the product. The less regular the crystals, the fewer voids there will be between crystals. Moreover, with less regular, relatively small crystals, crystalline fines are generally present which given rise to objectionable dust which makes handling the crystals in bulk a most unpleasant task. Of course, besides being essentially dust-free, uniform, large crystal masses have many other desirable properties; they can be filtered and washed more efficiently during processing, they have good flow characteristics, and they have a pleasing appearance—an important sales factor, particularly in the sale of big amounts of ammonium nitrate, ammonium sulfate, and nickel sulfate. Thus, there is a need for a simple, economical method of producing relatively large, well-defined crystals which may be grown from a supersaturated solution, and which are essentially free from dusty crystalline fines.

Again, relatively small crystals are highly susceptible to caking, even if the crystals are uniform. Thus there is also a need for a process which makes it unnecessary to provide the crystals with a coating agent such as is popular for many masses of small crystalline particles, for the purpose of retaining their free-flowing characteristics. It is common knowledge, for example, that table salt is coated with a very fine dust of magnesium carbonate. Icing sugar is coated with a tricalcium phosphate or corn flour. Other anti-caking agents that find use for industrial purposes include chalk, calcium sulfate, kaolin, diatomaceous earth and the like. Addition of anti-caking agents not only is an inconvenience and an economic burden, but generally introduces a significant level of an undesirable contaminant.

The importance of this process and its several benefits and advantages are unexpectedly due to the seeding of a saturated solution of inorganic salts and particularly ionic metal salts with an aqueous dispersion of sub-micron and micron-size particles of PTFE, as will be explained hereinafter.

SUMMARY OF THE INVENTION

It is therefore a general object of this invention to provide a new and improved process for growing geometrically well-defined and/or large crystals of inorganic and organometallic salts which are crystallizable from a saturated solution.

It is a more particular object of this invention to provide a new and improved process for seeding a saturated solution of an inorganic or organometallic salt with finely divided wettable particles of PTFE, which despite being a synthetic polymeric resin, surprisingly nucleates the solution to effect better crystallization than that effected without seeding, and yields crystals of the salt, essentially free of fines.

It is a more specific object of this process to seed a saturated solution of an ionic inorganic or organometallic salt with a colloidal suspension of fibrillatable PTFE to effect better defined or larger crystal growth of monoclinic, prismatic, triclinic, and cubic crystals, than that effected without seeding.

It is another specific object of this process to seed an aqueous solution of an ionic inorganic or organometallic salt with less than about 1 percent by weight, based on total solids precipitated, of finely divided wettable PTFE, to produce crystals having a predominantly monoclinic, prismatic or triclinic habit, which are characteristically better defined and/or larger than those crystals produced by crystallization without seeding.

It is still another object of this invention to provide a novel and unique ionic inorganic crystal seeded by a minute quantity of amorphous, solid, finely divided PTFE particles which unexpectedly initiate non-epitaxial growth, the occurence of which growth thereafter effectively propagates epitaxial growth in the normal habit of the inorganic crystal.

It is a particular object of this invention to provide inorganic ionic crystals grown by the initiation of non-epitaxial growth on an amorphous wettable PTFE resin particle, which crystals have approximately double the size of similar crystals grown under identical conditions, except for the seeding with PTFE.

A still further object of this invention is to provide a crystalline mass of inorganic crystals in the size range from about 80 U.S. standard mesh to about ¼-inch mesh, characterized by an absence of dusty fines, wherein a majority of the individual crystals have occluded therein at least one solid PTFE particle.

These and other objects, features and advantages of this process and the crystals grown thereby, will become apparent to those skilled in the art from the following description of preferred forms thereof and the examples set forth herein.

DETAILED DESCRIPTION OF PREFERRED EMBODIMENTS OF THE INVENTION

According to the process of this invention, an inorganic crystalline salt may be crystallized from an aqueous solution of the salt in the presence of finely divided polytetrafluoroethylene resin particles which are wettable by the solution.

In each embodiment of the instant invention, only water-wettable finely divided PTFE is used, such as water-wettable fibrillatable PTFE in the form of finely divided, solid particles commercially available as a colloidal aqueous dispersion concentrated to about 60% by weight of polymer having particles about 0.05 to about 0.5 microns in size, with average diameters of about 0.2 micron. Another type of fibrillatable PTFE, generally referred to as "fine powder", obtained by coagulation of the dispersion is less effective as a seeding agent because it is not wettable in aqueous solutions of inorganic salts. Most notable is the fact that finely divided solid forms of other particulate polyhalocarbons and polyolefins are ineffective as seeding agents to effect the growth of inorganic crystals which possess better appearance or larger dimensions than those grown without seeding, presumably because they are not water-wettable.

U.S. Pat. No. 2,559,752 discloses a process for forming an aqueous dispersion of colloidal water-wettable particles of PTFE resin. It is hypothesized that, were water-wettable finely divided forms of other synthetic polymeric resins available, they would be similarly useful as seeding agents which exhibit analogous characteristics of a colloidal aqueous dispersion of PTFE.

In general, inorganic crystals are grown from a saturated aqueous solution of the crystals in the presence of a small amount of PTFE resin in the range from about 0.1 to about 2 percent by weight, based on total solids precipitated from the solution. An amount of PTFE in excess of 2 percent by weight may be added, but it will be apparent that, particularly where relatively large crystals, greater than about 100 mesh, are to be grown, there is no economic justification for the addition of a substantially larger amount of PTFE than is required to effect the desired superior crystal growth. Seeding with PTFE appears generally to have no significant effect on yield of crystals on a weight basis, as compared with an unseeded solution.

Since, in most instances, the yield of crystals from a preselected solution to be seeded with PTFE is already known, the amount of PTFE to be added may be estimated, from one batch to another, with some accuracy.

It is hypothesized that the process of this invention is characterized by the initiation of crystal growth, nonepitaxially, by one individual microscopic or submicroscopic particle of PTFE, or a small agglomerate of plural, proximately disposed particles. This hypothesis as to non-epitaxial growth is based on the fact that a PTFE polymer particle has no crystalline lattice and therefore cannot initiate epitaxial growth of any crystal. Crystal growth initiated in this non-epitaxial manner is thereafter propagated epitaxially in a particular habit, or characteristic lattice, in which the crystal would normally grow if it were not seeded with a water-wettable polymer particle.

With the foregoing understanding of the mechanism of the process, it is preferable to provide an optimum amount of wettable polymer which theoretically corresponds numerically to at least about the number of crystals grown from solution, assuming it is desirable to have all the crystals grown in a geometrically better-defined or larger physical form than they would otherwise acquire. By geometrically well-defined is meant that individual crystals are essentially free of stunted growth and notably free of irregular growth on any of the crystal faces. The geometrically better-defined growth of PTFE seeded crystals is particularly apparent when compared to the shape of crystals grown without seeding. Most unexpectedly the size of crystals grown by seeding with fibrillatable wettable PTFE particles of the preferred size range is generally more uniform and often larger than crystals obtained by seeding with fine isomorphous crystals. It will be expected that a substantially lesser amount than the optimum amount of PTFE may not yield as desirable a size distribution, though the mass of crystals grown may still be, characteristically, essentially free of crystalline fines having a size range less than about 325 mesh.

Crystals grown by the instant process characteristically contain at least one occluded PTFE particle. Additional occluded PTFE particles may be present within the crystal or upon a face of the crystal, but irrespective of the location of additional occlusions, there appears to be no evidence of a stunting of growth because of the occlusions of PTFE. It will be recognized that occlusions of individual particles of PTFE are most difficult to see even under high magnification. The presence of the PTFE particles in or on crystals grown with PTFE seeding, is evidenced by the formation of a residue of PTFE when these crystals are re-dissolved.

The particular manner in which crystallization is effected is not of critical importance and any conventional crystallization process will benefit from this invention. For example, a single-effect evaporator, working at atmospheric pressure, may have added to it an effective amount of colloidal PTFE particles which are uniformly distributed therein. The solution in the evaporator remains clear as it is concentrated, and, after transfer to a crystallizer, deposits crystals as the solution cools. In a similar manner, multiple-effect evaporators may also be seeded with PTFE particles, and yield larger and more attractive crystals than solutions which are not so seeded.

Alternatively, colloidal PTFE particles may be added to the crystallizer before crystals begin to be deposited, and the solution slowly agitated by a rotating arm or propeller mixer. After crystallization, the molten liquor is run off and the wet crystals recovered for drying.

Where particularly large and well-defined crystals are to be grown, the solution may be seeded with crystals which have been previously seeded with PTFE particles. Such crystals may contain PTFE particles occluded on or near their faces, in addition to one or more particles occluded within the lattice. When a solution is seeded with PTFE preseeded crystals additional growth occurs epitaxially in accordance with well-recognized patterns of crystal growth. The occluded PTFE particles in the preseeded crystals appear to have no unusual effects on further growth, but most surprisingly, PTFE particles at or near the surface of the crystal faces appear to aid, rather than hinder, crystal growth. A further additional quantity of PTFE particles may be used, if desired, in those instances where an additional beneficial effect is obtained by such addition, as for example, noticeably faster crystallization.

The crystallization process of this invention is particularly effective in the growth of ionic inorganic and organometallic salts which are crystallizable from saturated aqueous solutions, irrespective of the characteristic habit in which they are normally formed. In those instances where a salt is crystallizable in more than one habit from an unseeded saturated solution, seeding with PTFE particles appears to have no noticeable effect on the formation of crystals with different habits, except that the crystals are larger and have better appearance. This crystallization process is most particularly directed to the growth of monoclinic, prismatic, triclinic and cubic crystals which may be formed and grown in the presence of less than two percent by weight of colloidal PTFE particles, based on total solids precipitated from solution, and more preferably in the presence of from about 0.01 to about 1.0 percent by weight PTFE.

Ionic inorganic salts which may be grown by the process of this invention include the salts of metals forming cations from Groups I, II, III, VI, and VIII including the salts of mixed metals thereof for example, potassium aluminum sulfate, potassium dichromate and the like.

Ionic organometallic salts which may be grown by the process of this invention include the metal salts particularly of Groups I or VIII, of the lower carboxylic acids having less than six carbon atoms such as nickel and sodium acetate.

The following examples are by way of illustration only, and this invention is not limited by the particular inorganic salts and organometallic salts described hereinbelow.

EXAMPLE 1

A one-liter solution of nickel acetate is prepared by adding 356 gms of $Ni(CH_3COO)_2 \cdot 4H_2O$ and 84 gms. glacial acetic acid to 600 ml. water. A temperature of 80°–90°C. is maintained to ensure dissolution of the organometallic salt and additional water is added to bring the volume to one liter. A very small, but noticeable amount of solid would not dissolve and is removed by filtration through a Buchner funnel. The filtrate has a specific gravity of 1.145 at 80° C.

Each of two 250 ml. portions of the solution are seeded with 2.66 g. of Teflon* T-30 aqueous colloidal dispersion (about 1.6 g. of PTFE solids) of PTFE, and 1.6 g. of Teflon* T-6 PTFE fine powder respectively. A third 250 ml. portion is maintained as a control and contains no PTFE.

*Registered Trademark of the E. I. DuPont de Nemours Co.

Each 250 ml. portion at about 80° C. is contained in a tall 300 ml. beaker provided with a Teflon coated stirring bar. Each portion is stirred slowly and continuously. It is preferred to make the additions of PTFE slowly while stirring to maintain the polymer particles as homogeneously dispersed as possible. The T-6 fine powder is not wettable and an attempt to pre-wet the powder with methanol was ineffective to provide a homogeneous dispersion.

Stirring of the hot solutions is continued overnight, and the temperature falls to room temperature of about 23° C. A mass of crystals crystallizes from each of the three portions which are further chilled to about 15° C. in a water bath while stirring is continued for a period of about two hours. Each portion is filtered through a Buchner funnel until relatively dry and the mass of crystals obtained from each portion are weighed and thereafter dried in an oven at 100° C. for thirty minutes while moderate shear is applied to each mass of crystals while it is drying. The crystals are prismatic.

|  | Funnel dry wt. gms. | Oven dry wt. gms. | % loss after drying |
|---|---|---|---|
| Control | 74.1 | 59.2 | 20.1 |
| Portion with T-30 *Teflon | 67.3 | 59.6 | 11.4 |

-continued

| | Funnel dry wt. gms. | Oven dry wt. gms. | % loss after drying |
|---|---|---|---|
| Portion with T-6 *Teflon | 83.4 | 69.4 | 16.8 |

*Registered Trademark

A comparison of the appearance of the dried crystals indicates that the crystals with T-30 are less white and more green than the others. In addition the crystals with T-30 flowed more freely and were remarkably free of fines thus permitting the mass to be handled without a mask. By contrast, the crystals obtained from the control are characteristically dusty and the crystals with T-6 show only moderate improvement.

Microscopic examination of the crystal masses indicates that the crystals with T-30 are geometrically better defined and larger than the crystals of either the control or the crystals grown in the presence of T-6 fine powder. Control crystals range in size up to 250 microns, the majority being between 40–150 $\mu$. Crystals from the T-30 treated portion range in size up to 1300 $\mu$ the majority being in the range from 100–400 microns.

It will be apparent that the low percentage loss of moisture after drying the crystals containing T-30 produces an economic benefit in that the dried crystals may be obtained more quickly and therefore at less cost.

EXAMPLE 2

Potassium dichromate crystals are obtained from a control aqueous solution as follows:

A. 75 gms. of potassium dichromate are dissolved in 100 ml. water at 90° C. The hot solution is filtered through a Buchner funnel to remove insoluble impurities. The hot solution is stirred slowly and continuously while depositing crystals and cooling overnight to room temperature. It is thereafter cooled to 10°C. in an ice bath. The crystals are separated from solution by filtering through a Buchner funnel until relatively dry and thereafter dried for 5 hours at about 75° C. under vacuum.

B. In the same manner as described immediately hereinabove another potassium dichromate solution is prepared and maintained at 90° C. while 2.5 gms. of Teflon T-30* dispersion (about 1.5 gms. PTFE) is added and homogeneously dispersed therein. The solution containing T-30 PTFE is permitted to deposit and grow crystals while cooling overnight to room temperature. It is thereafter chilled in an ice bath at 10° C., the crystals separated and dried at 75° C. for 5 hours under vacuum.

Microscopic examination of the crystals obtained from the control and the T-30 treated solution discloses that the latter are approximately twice as large. There is no visual indication of the presence of PTFE particles in or on the crystals, though agglomerates of PTFE are observed. These agglomerates of PTFE appear to be excess PTFE particles which were not occluded by the crystals. The crystals are triclinic.

EXAMPLE 3

In a manner analogous with that described in Example 2 hereinabove, potassium aluminum sulfate crystals of relatively larger size and better geometrical definition than unseeded alum crystals, are grown when seeded with wettable PTFE particles of T-30 dispersion. The crystals are monoclinic.

EXAMPLE 4

A finely divided non-fibrillatable powder, of Whitcon No. 5 PTFE is treated with a conventional wetting agent to render it wettable. In a manner analogous to that described in Example 2A hereinabove, a nickel acetate solution is prepared and treated with the treated, wettable, non-fibrillatable PTFE in the same amount, that is, 1.5 gm. PTFE in 75 gms. of potassium dichromate. Crystals recovered have PTFE particles occluded therein and are better defined and larger than crystals obtained in Example 2A.

Modifications, changes, and improvements to the preferred forms of the invention herein disclosed, described, and illustrated occur to those skilled in the art who come to understand the principles and precepts thereof. Accordingly, the scope of the patent to be issued hereon should not be limited to the particular embodiments of the invention set forth herein, but rather should be limited by the advance by which the invention has promoted the art.

What is claimed is:

1. A crystal of an inorganic ionic metal salt crystallizable from an aqueous solution of said salt, said crystal consisting essentially of said inorganic ionic metal salt and at least one particle of water-wettable polytetrafluoroethylene polymer in a size range from about 0.05 $\mu$ to about 0.5 $\mu$, formed in an aqueous suspensoid, said particle being occluded in said crystal which is formed in a size range from about 80 U.S. Standard mesh to about ¼ inch mesh.

2. The crystal of claim 1 wherein said inorganic ionic metal salt has a crystal habit selected from the group consisting of monoclinic, prismatic and triclinic.

3. The crystal of claim 1 wherein said inorganic ionic metal salt includes a cation of a metal selected from the group consisting of metals of Groups I, II, III, VI and VIII of the Periodic Table.

* * * * *